US008278459B2

(12) United States Patent
Vollhardt et al.

(10) Patent No.: US 8,278,459 B2
(45) Date of Patent: Oct. 2, 2012

(54) UV-FILTER COMPOUNDS

(75) Inventors: Jürgen H. Vollhardt, Ramlinsburg (CH); Yevgen Blyumin, Füllingsdorf (CH); Alexander Poschalko, Birsfelden (CH)

(73) Assignee: DSM IP Assets B.V., Heerlen (NL)

( * ) Notice: Subject to any disclaimer, the term of this patent is extended or adjusted under 35 U.S.C. 154(b) by 260 days.

(21) Appl. No.: 12/531,945

(22) PCT Filed: Feb. 28, 2008

(86) PCT No.: PCT/EP2008/001591
§ 371 (c)(1),
(2), (4) Date: Sep. 18, 2009

(87) PCT Pub. No.: WO2008/122329
PCT Pub. Date: Oct. 16, 2008

(65) Prior Publication Data
US 2010/0119462 A1    May 13, 2010

(30) Foreign Application Priority Data
Mar. 19, 2007    (EP) .................................. 07005613

(51) Int. Cl.
*C07D 235/04* (2006.01)
*C07D 263/54* (2006.01)
*C07D 277/62* (2006.01)
*A61Q 17/00* (2006.01)

(52) U.S. Cl. ..................... 548/203; 548/217; 548/304.4; 252/401; 252/403; 424/59; 424/401

(58) Field of Classification Search .................. 548/203, 548/217, 304.4; 252/403, 401; 424/59, 401
See application file for complete search history.

(56) References Cited

U.S. PATENT DOCUMENTS 7,863,478 B2 * 1/2011 Carola et al. .................. 560/203

FOREIGN PATENT DOCUMENTS

| WO | WO 99/03841 | 1/1999 |
| WO | WO 99/31263 | 6/1999 |
| WO | WO 2006/018104 | 2/2006 |

OTHER PUBLICATIONS

International Search Report for PCT/EP2008/001591, mailed Jul. 30, 2008.
Written Opinion of the International Searching Authority for PCT/EP2008/001591, mailed Jul. 30, 2008.
Xu, Y. Y. et al., "Design of Organocatalysts for Asymmetric Direct Syn-Aldol Reactions", Organic Letters, vol. 9, No. 21, (Oct. 11, 2007), pp. 4247-4249.
Cox, R.J. et al., "Acyl palladium species in synthesis: single-step synthesis of α,β-unsaturated ketones from acid chlorides", Organic and Biomolecular Chemistry, vol. 5, No. 2, (Jan. 21, 2007).
Ramasastry, S.S.V. et al., "Direct Catalytic Asymmetric Synthesis of *anti*-1, 2-Amino Alcohols and *syn*-1,2-Diols through Organocatalytic *anti*-Mannich and *syn*-Aldo Reactions", Journal of the American Chemical Society, vol. 129, No. 2, (Dec. 20, 2006), pp. 288-289.
Gu, Q. et al., "(2S,5S)-Pyrrolidine-2,5-dicarboxylic acid, an efficient chiral organocatalyst for direct aldol reactions", Tetrahedron: Asymmetry, vol. 16, No. 10, (Jun. 19, 2006), pp. 1537-1540.
Korber, K. et al., "A Novel Strategy for the Convergent Synthesis of 1,3,5 . . . -Polyols: Enone Formation, Asymmetric Dihydroxylation, Reductive Cleavage, Hydride Addition", SNYLETT, No. 19, (2005), pp. 2905-2910.
Chenevert, R. et al., "Chemoenzymatic Synthesis of the Microbial Elicitor (-)-Syringolide via a Fructose 1,6-Diphosphate Aldolase-Catalyzed Condensation Reaction", Chemical Society, vol. 65, (Jan. 1, 2000), pp. 4529-4531.
Chenevert, R. et al., "Use of aldolases in the synthesis of non-carbohydrate natural products. Stereoselective synthesis of aspicilin C-3—C-9 fragment", Canadian Journal of Chemistry, vol. 75, No. 1, (1997), pp. 68-73.
Kang, S.K. et al., "Complete Reverse Regioselection in Wacker Oxidation of Acetonides and Cyclic Carbonates of Allylic Diols", Journal of Organic Chemistry, vol. 60, No. 15, (1995), pp. 4678-4679.
Bednarski, Mark D. et al, "Rabbit Muscle Aldolase as a Catalyst in Organic Synthesis", Journal of the American Chemical Societya, vol. 111, (Jan. 1, 1989), pp. 627-635.
Database CAPLUS [Online] Chemical Abstracts Services, (Aug. 1, 2007), Accession No. 2007:834935, 2 pages.
Database CAPLUS [Online] Chemical Abstracts Services, (Jul. 25, 2007), Accession No. 2007:808570, 2 pages.
Database CAPLUS [Online] Chemical Abstracts Services, (May 9, 2007), Accession No. 2007:502981, 1 page.
Database CAPLUS [Online] Chemical Abstracts Services, (Apr. 2, 2007), Accession No. 2007:362178, 1 page.
Database CAPLUS [Online] Chemical Abstracts Services, (Feb. 28, 2006), Accession No. 2006:180191, 2 pages.
Database CAPLUS [Online] Chemical Abstracts Services, (Feb. 20, 2006), Accession No. 2006:156534 1 page.
Database CAPLUS [Online] Chemical Abstracts Services, (Dec. 25, 2005), Accession No. 2005:1338289, 2 pages.
Database CAPLUS [Online] Chemical Abstracts Services, (Nov. 7, 2003), Accession No. 2003:875249, 2 pages. Database CAPLUS [Online] Chemical Abstracts Services, (Nov. 21, 2002), Accession No. 2002:881454.
Database CAPLUS [Online] Chemical Abstracts Services, (Jun. 11, 1994), Accession No. 1994:298152, 1 page.
Database CAPLUS [Online] Chemical Abstracts Services, (Apr. 22, 2001), Accession No. 196:117692, 1 page.
International Preliminary Report on Patentability, PCT/EP2008/001591, Sep. 22, 2009.

* cited by examiner

*Primary Examiner* — Venkataraman Balasubramanian
(74) *Attorney, Agent, or Firm* — Nixon & Vanderhye P.C.

(57) ABSTRACT

The present invention provides novel diol compounds, novel cosmetic or dermatological sunscreen compositions containing these compounds and the use of the novel compounds as UV-filters. The compounds are particularly advantageous, because they adhere to the skin and therefore provide sunscreen protection for a prolonged period of time.

16 Claims, No Drawings

UV-FILTER COMPOUNDS

This application is the U.S. national phase of International Application No. PCT/EP2008/001591 filed 28 Feb. 2008, which designated the U.S. and claims priority to Europe Application No. 07005613.0 filed 19 Mar. 2007, the entire contents of each of which are hereby incorporated by reference.

The present invention relates to novel diol compounds, to novel cosmetic or dermatological sunscreen compositions containing these compounds and the use of the novel compounds as UV-filters, in particular for photoprotecting human skin and/or hair against UV radiation, in particular solar radiation.

There's a constantly increasing need for sunscreen protection agents in a population which is exposed to an increasing amount of damaging sunlight. Repetitive sun exposure can result in skin changes known as photo-aged skin. The clinical changes that are seen in photo-aged skin differ from those of normally aged skin in the sunlight protected sides of the body. Among damaging results of extensive sun exposure of the skin there is increased wrinkling, elastosis, pigmentary changes, precancerous and cancerous skin lesions.

Many sunscreen chemicals have been developed in the past protecting against the harmful effect of UV-A (320-400 nm) and/or UV-B (290-320 nm) wavelength and even shorter wavelengths (UV-C). These chemicals are usually incorporated either alone or in combination with each other in cosmetic or pharmaceutical preparations which are widely known and used.

There are many requirements on UV-filter compounds. In particular an UV-filter compound should not be able to penetrate the skin of humans because this might cause unpleasant or harmful reactions. It goes without saying that an UV-filter compound should also not be harmful to skin and be compatible even with sensitive skin. Of course, a high UV-filter activity is also a requirement for a good UV-filter compound. Advantageously, an UV-filter compound should also provide long-term protection which requires a good adhesion to human skin and hair. It is further advantageous if a UV-filter compound also provides additional benefits like photostabilization of a composition or a component of a cosmetic formulation, boosting of the UV protection performance, skin moisturization and skin tanning.

A high number of UV filter compounds have been developed which have a high UV filter activity and are compatible with skin and do not penetrate the human skin in significant amount. However, those UV filter compounds generally lack a good adhesion to the human skin and hair. After application they are easily removed by clothing or after contact with water, e.g. during bathing or swimming. Further those UV-filter compounds often cannot provide additional benefits like photostabilization of a composition or a component of a cosmetic formulation, boosting of the UV protection performance, skin moisturization and skin tanning.

Thus, many of the known UV-filtering compounds cannot provide the desirable long-term protection. An UV-filter compound should be able to attach itself to the skin for a prolonged period of time so that it is not washed or wiped away soon after application, in addition to the above listed properties.

There are some suggestions in the prior art, how to improve the adherence of organic molecules to human skin.

Combinations of UV-filter compounds with malein imides and maleic acid derivatives are e.g. disclosed in WO 95/30646. α-Hydroxyalkyl derivatives are known e.g. from WO 93/16026 and α,β-unsaturated ketones which are chemically connected to UV-filters or antioxidants are disclosed in U.S. Pat. No. 6,613,341. Mono- and dihydroxyacetone esters as well as 3-hydroxy-2-oxypropylamids containing UV-filter compounds are disclosed in WO 2006/018104.

WO 01/06829 discloses reactive groups which are suitable to bind agents to proteinaceous material such as body tissue. The agents are not particularly restricted and a wide range of possible compounds including e.g. sunscreen agents, anti-foaming agents, anti-nerve gas agents etc. are mentioned. When the agents are sunscreen agents according to WO 01/06829 these sunscreen agents are generally in the form of microparticles. The reactive group which is used for binding the agents/microparticles to body tissue is not particularly limited either and a high number of reactive groups are explicitly mentioned, some of which comprise reactive carbonyl groups while others comprise reactive Michael-acceptors. A particular drawback of the suggested binding strategies is that these may also lead to skin sensitisation reactions.

There is no disclosure in WO 01/06829 that a certain reactive group such as a group R—C(O)—CH(OH)—CH(OH)— can effectively bind UV filter agents to skin without impairing the compatibility of the UV filter compound with the skin and without increasing the penetration ability of the UV filter compound through the skin.

The problem to be solved by the present invention is providing novel UV-filter compounds that do not only have a high UV filter activity, a good compatibility with skin and low or none penetration into the skin but which in addition have excellent adhesion to human skin.

The solution to this problem is based on the finding that chemical structures which are known to act as UV-filters can easily be coupled to a chemical group having the formula R—C(O)—CH(OH)—CH(OH)— and that this chemical group provides excellent adhesion of the UV filter structure to the skin without incurring negative effects on the compatibility with skin or causing penetration into the skin.

The present invention therefore provides a compound of formula I

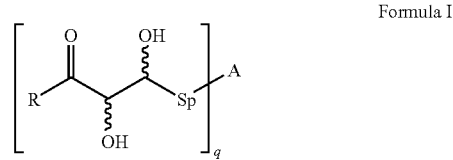

Formula I wherein
R is $C_1$-$C_{24}$-alkyl, optionally substituted with up to 3 hydroxyl groups, a residue —$(CH_2)_n$—Y or a residue $(CH_2)_n$-Sp-A wherein the —$(CH_2)_n$— moieties can optionally be substituted with up to 3 hydroxyl groups A is a substituent that absorbs light in the UV-range and has a conjugated π electron system of at least 4π electrons Sp is a bond or a linear or branched residue —$(CH_2)_n$—, —$(CH_2)_n$—$C_6H_4$—$(CH_2)_o$—, —$(CH_2)_n$—C(=O)—$(CH_2)_o$—, —$(CH_2)_n$—C(=O)—$(CH_2)_o$—X—$(CH_2)_p$— or —$(CH_2)_n$—X—$(CH_2)_p$—

X is O, $NR^1$, $S(O)_m$ $R^1$ is H, $C_{1-24}$-alkyl, optionally substituted with up to 3 hydroxyl groups, or —$(CH_2)_n$—Y Y is selected from $C_{1-24}$-alkyl, $C_3$-$C_{10}$-cycloalkyl and $C_6$-$C_{10}$-Aryl, unsubstituted or substituted with 1-3 substituents independently selected from hydroxyl groups and $C_1$-$C_6$-alkyl groups m is a number selected from 0, 1, 2 n, o and p are whole numbers independently selected from the range of 0-24
q is an integer of 1, 2 or 3
wherein different residues R, X, Sp, $R^1$, A and Y can have the same or different meanings.

The substituents A that absorb light in the UV-range comprise all groups which absorb light (have an absorption maximum) in the range of wavelength 400-320 nm (UV-A) and/or 320-290 nm (UV-B) or even of shorter wavelengths (UV-C) and which are or can be used as chemical UV filters. Such substituents have a conjugated π electron system of at least 4 π electrons.

The substituents A are e.g. residues of chromophores belonging to the groups of acrylates, p-aminobenzoates, camphor derivatives (such as of benzylidene camphor type), cinnamates, benzophenones, esters of benzalmalonic acid, esters of 2-(4-ethoxy anilinomethylene)propandioic, imidazole derivatives, (benz)azole derivatives, salicylates, triazine derivatives, triazol derivatives, dibenzoylmethanes, amino substituted hydroxybenzophenones, anthranilates, 1,4-dihydropyranes, chromone-, isoflavone- and flavone derivatives, quinoxaline derivatives and others representing state of the art and known to those skilled in the art to be highly active.

Examples for acrylates include 2-ethylhexyl 2-cyano-3,3-diphenylacrylate (octocrylene, PARSOL® 340) and ethyl 2-cyano-3,3-diphenylacrylate;

Examples for p-aminobenzoates include 4-amino benzoic acid, 4-aminobenzoic acid-2,3-dihydroxypropylester, 4-(bis (2-hydroxypropyl)amino)benzoic acid ethyl ester, 4-(dimethylamino)benzoic acid-2-ethylhexylester (e.g. Eusolex® 6007) and ethoxylated 4-aminobenzoic acid ethyl ester (e.g. Uvinul® P25).

Examples for camphor derivatives include 4-methyl benzylidene camphor (PARSOL® 5000), 3-benzylidene camphor, camphor benzalkonium methosulfate, polyacrylamidomethyl benzylidene camphor, sulfo benzylidene camphor, sulfomethyl benzylidene camphor and terephthalidene dicamphor sulfonic acid;

Examples for cinnamates include octyl methoxycinnamate (PARSOL® MCX), ethoxyethyl methoxycinnamate, diethanolamine methoxycinnamate (PARSOL® Hydro) and isoamyl methoxycinnamate.

Examples for benzophenones include benzophenone-3, benzophenone-4, 2,2',4,4' tetrahydroxy-benzophenone and 2,2'Dihydroxy-4,4' dimethoxybenzophenone;

Examples for esters of benzalmalonic acid include di(2-ethylhexyl) 4-methoxybenzalmalonate.

Examples for esters of 2-(4-ethoxy anilinomethylene)propandioic acid include 2-(4-ethoxy anilinomethylene)propandioic acid diethyl ester as described in the European Patent Publication EP 0895 776;

Examples for imidazole derivatives include substituted 2-phenylbenzimidazole derivatives, 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts and diethanolamine salts.

Examples for (benz)azole derivatives include substituted 2-phenylbenzoxazole derivatives, 2,4-bis[5-(1-dimethylpropyl)benzoxazol-2-yl(4-phenyl)imino]-6-(2-ethylhexyl) imino-1,3,5-triazine (Uvasorb K 2A) described in JP 55064578 and EP 1123934.

Examples for salicylate derivatives include isopropylbenzyl salicylate, benzyl salicylate, butyl salicylate, octyl salicylate (NEO HELIOPAN OS), isooctyl salicylate or homomethyl salicylate (homosalate, HELIOPAN);

Examples for triazine derivatives include octyl triazone (UVINUL T-150), dioctyl butamido triazone (UVASORB HEB).

Examples for triazol derivatives include benzotriazoles such as 2-(2-hydroxy-5-methylphanyl)benzotriazol, 2,2'-methylene-bis-(6-(2H-benzotriazole-2-yl)-4-(1,1,3,3,-tetramethylbutyl)-phenol (TINOSORB M) as well as triazols described in EP-A-893119.

Examples for dibenzoylmethane derivatives include compounds such as 4-tert. butyl-4'-methoxydibenzoyl-methane (PARSOL® 1789), dimethoxydibenzoylmethane and isopropyldibenzoylmethane;

Examples for Amino substituted hydroxybenzophenones include compounds such as 2-(4-Diethylamino-2-hydroxybenzoyl)-benzoic acid hexyl ester as described in the European Patent Publication EP 1046391.

Examples for 1,4-dihydropyranes, chromone-, isoflavone- and flavones include their derivatives as well as compounds described in WO 2006128562.

Examples for quinoxaline derivatives and quinoxaline-containing heterocyclic compounds are described in DE 10111728.

Particularly preferred examples of substituent A are the following:

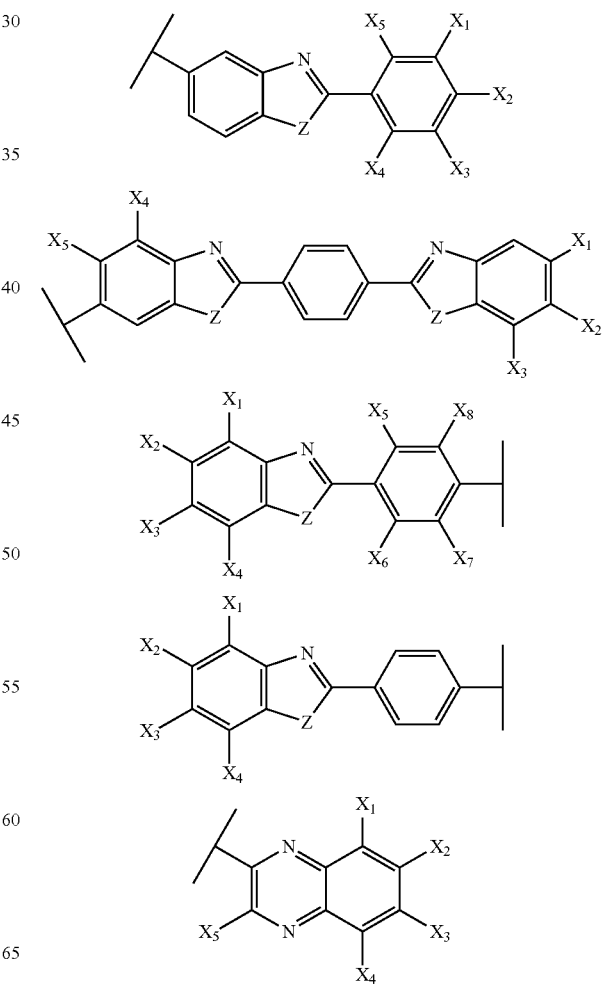

US 8,278,459 B2
5
-continued
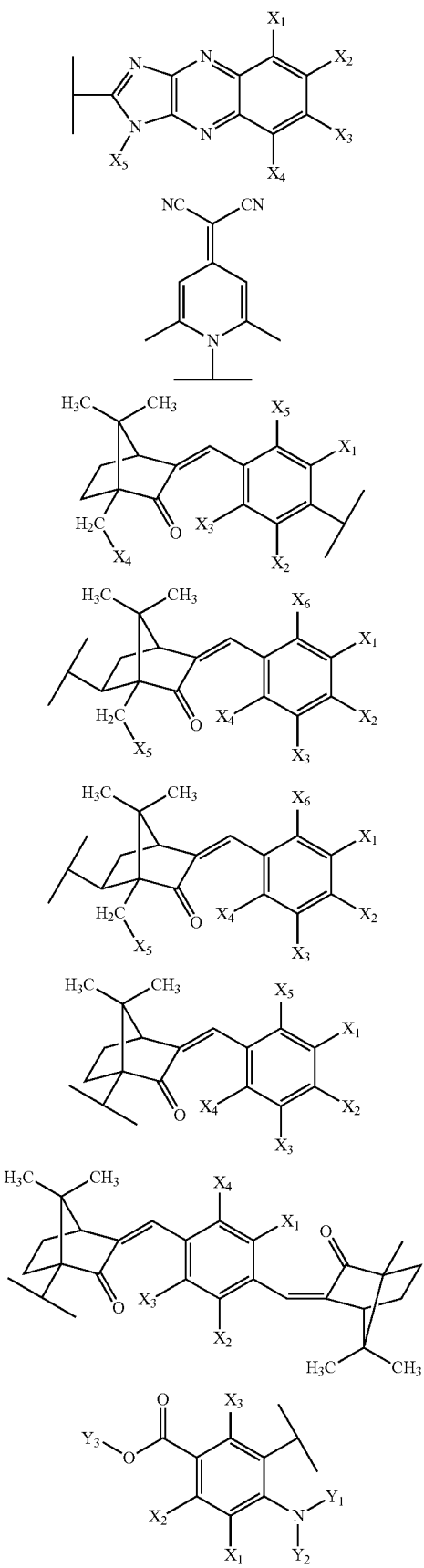
6
-continued
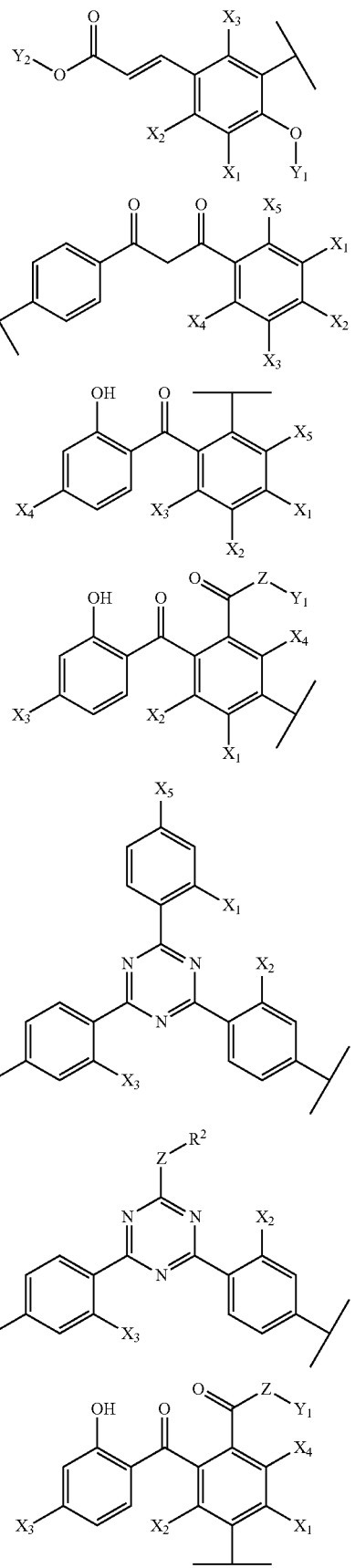

-continued

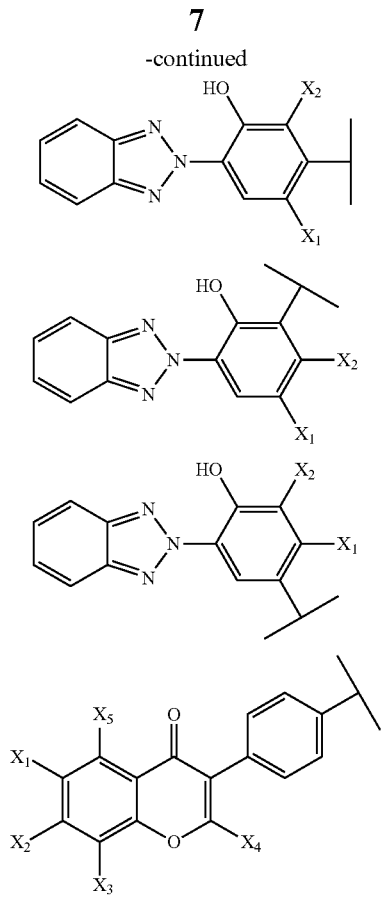

wherein $X_1$, $X_2$, $X_3$, $X_4$, $X_5$, $X_6$, $X_7$ and $X_8$ are independently from each other H, OH, $C_{1-24}$-alkyl, unsubstituted or substituted with up to 3 hydroxyl groups or residues Y, $C_{1-24}$-alkyl-C(O)O, C(O)O—$C_{1-24}$-alkyl, $C_{1-8}$-alkoxyl, $S(O)_r$OH or monoglycosidyl.

Y is defined as above,

Z is selected from NH, $NR^2$, O and S, each residue $R^2$ is independently selected from H, $C_{1-24}$-alkyl, aryl, heteroaryl or Y, $Y_1$, $Y_2$ and $Y_3$ are independently H or $C_{1-24}$-alkyl and r is 1 or 2.

Most preferred substituents A are

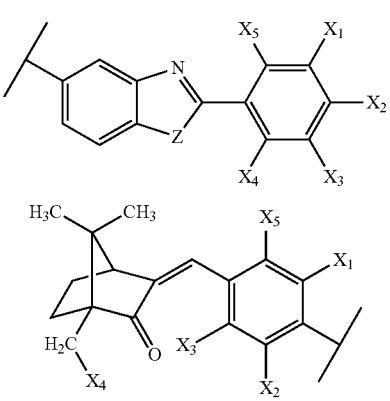

-continued

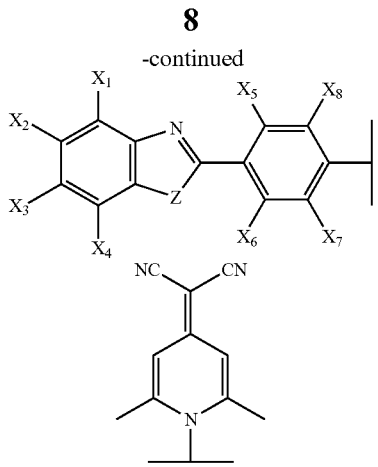

wherein $X_1$, $X_2$, $X_3$, $X_4$, $X_5$ $X_6$, $X_7$ and $X_8$ and Z are as defined above.

In the definitions of the formulae for substituent A residue Z is preferably NH or O and $R^2$ is preferably H or $C_1$-$C_6$-alkyl.

In the definitions of the formulae for the substituent A residues $X_1$, $X_2$, $X_3$, $X_4$, $X_5$, $X_8$, $X_7$ and $X_8$ are preferably independently of each other H or $C_1$-$C_6$-alkyl, $S(O)_r$OH, more preferably only one of the residues $X_1$, $X_2$, $X_3$, $X_4$, $X_5$, $X_6$, $X_7$ and $X_8$ in a substituent is different from H and most preferably all residues $X_1$, $X_2$, $X_3$, $X_4$, $X_5$, $X_6$, $X_7$ and $X_8$ are H.

In the definitions of the formulae for substituent A, residues $Y_1$, $Y_2$ and $Y_3$ are preferably independently H or $C_1$-$C_6$-alkyl, more preferably $C_1$-$C_6$-alkyl.

Residue R can furthermore contain an additional UV filter substituent A which is bonded over a group $(CH_2)_n$-Sp-A wherein the —$(CH_2)_n$— moiety can optionally be substituted with up to 3 hydroxyl groups. Preferably, R is $C_1$-$C_{24}$-alkyl unsubstituted or substituted with up to three hydroxyl groups, still more preferably R is $C_{1-10}$-alkyl unsubstituted or optionally substituted with up to three, more preferably one hydroxyl group and particularly preferred is residue R a $C_1$-$C_6$-alkyl group such as methyl, ethyl, n-propyl, isopropyl, n-butyl, isobutyl or tertiary-butyl, which group is preferably substituted by one hydroxyl group, and is in particular a hydroxymethyl group.

Residue R can also be a residue —$(CH_2)_n$—Y wherein n is an integer in the range of 0-24, more preferably 0-10 and most preferably in the range of 1-6.

Residue Sp is a bond or a linear or branched linking group selected from —$(CH_2)_n$—, —$(CH_2)_n$—$C_6H_4$—$(CH_2)_o$—, —$(CH_2)_n$—C(=O)—$(CH_2)_o$—, —$(CH_2)_n$—C(=O)—$(CH_2)_o$—X—$(CH_2)_p$— or —$(CH_2)_n$—X—$(CH_2)_p$—, preferably, Sp is a bond or a group —$(CH_2)_n$—, most preferably Sp is a bond.

In the above formulae n, o and p are independently selected from the range of 0-24, more preferably in the range of 1-24, more preferably in the range of 1-10, most preferably in the range of 1-4, and are e.g. 1, 2, 3 or 4.

In the above formulae residue X is O, $NR^1$ or $S(O)_m$ wherein m is 0, 1 or 2, preferably 1 or 2. Preferably, X is O.

Residue $R^1$ in the above formulae is H, $C_{1-24}$-alkyl, optionally substituted with up to three hydroxyl groups or residue $(CH_2)_n$—Y. If residue $R^1$ is a $C_1$-$C_{24}$-alkyl group optionally substituted with up to three hydroxyl groups or a residue —$(CH_2)_n$—Y, the preferred residues $R^1$ are the same as disclosed above for residue R. n is preferably as defined above in the definition of residue R.

Y is selected from $C_1$-$C_{24}$-alkyl, $C_3$-$C_{10}$-cycloalkyl and $C_6$-$C_{10}$-aryl, unsubstituted or substituted with 1-3 substituents independently selected from hydroxyl groups and $C_1$-$C_6$-alkyl groups. Most preferably Y is a $C_6$-$C_{10}$-aryl group, unsubstituted or substituted with 1-3 substituents, preferably with one substituent selected from $C_1$-$C_6$-alkyl groups. Most preferably Y is a phenyl group unsubstituted or substituted with 1 or 2 $C_1$-$C_6$-alkyl groups.

In the above formulae index q is an integer of 1, 2 or 3, preferably q is 1 or 2, most preferably q is 1.

The terms "aryl" and "heteroaryl" as used in the present application include monocyclic and polycyclic unsaturated aromatic ring structures having 6 to 18 carbon atoms, preferably 6 to 10 carbon atoms, with "aryl" referring to those that are carbocycles and "heteroaryl" referring to those that are heterocycles. A heterocycle preferably contains 1 to 5 heteroatoms, more preferably 1 to 3, e.g. 1 or 2 heteroatoms. The heteroatoms are preferably selected from O, S and N. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, 1,2,3-triazinyl, 1,2,4-oyadiazolyl, 1,3,4,-oxadiazolyl, 1-H-tetrazol-5-yl, indolyl, quinolinyl, benzothiophenyl (tianaphthenyl), furanyl, thiophenyl, imidazolyl, oxazolyl, isoxazolyl, thiazolyl, triazolyl, tetrazolyl, isoquinolinyl, acridinyl, pyrimidinyl, benzimidazolyl, benzofuranyl, and the like.

If in the above formulae more than one residue R, more than one residue X, more than one residue Y, more than one residue $R^1$, more than one residue Sp or more than one residue A appears, those residues can have the same or different meanings.

Preferred are also combinations of the above preferred residues. For example a combination wherein R is $C_1$-$C_6$-alkyl which is preferably substituted by one hydroxyl group, in particular wherein R is a hydroxymethyl group, A is a substituent of the formula

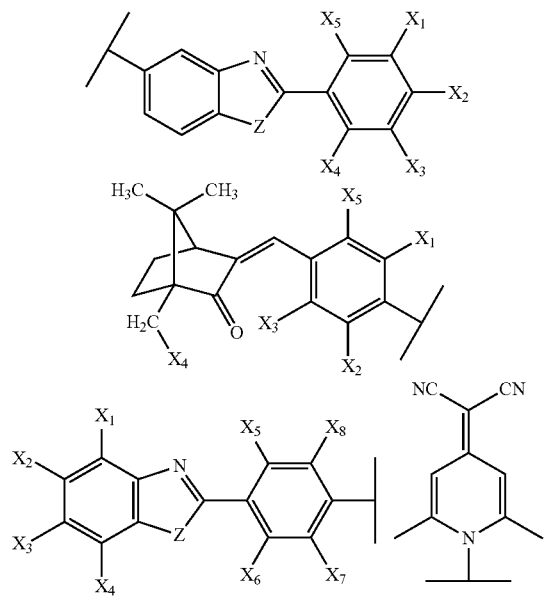

wherein $X_1$, $X_2$, $X_3$, $X_4$, $X_5$, $X_6$, $X_7$ and $X_8$ are independently of each other H or $C_1$-$C_6$-alkyl or $S(O)_r$OH, more preferably H, Z is NH or O, Sp is a bond and q is 1 or 2, more preferably 1, and r is 1 or 2 are also preferred in the present specification.

All other combinations of preferred and more preferred residues indicated above are also explicitly preferred according to the present application.

Particularly preferred are e.g. compounds wherein R is $C_1$-$C_6$-alkyl, optionally substituted with up to 3 hydroxyl groups, preferably substituted by one hydroxyl group, in particular a hydroxymethyl group, —$(CH_2)_n$—Y or a group $(CH_2)_n$-Sp-A, wherein —$(CH_2)_n$— is optionally substituted by up to 3 hydroxyl groups, Sp is a bond or a group —$(CH_2)_n$—, —$(CH_2)_n$—$C_6H_4$—$(CH_2)_o$—, —$(CH_2)_n$—C(=O)—$(CH_2)_o$—, —$(CH_2)_n$—C(=O)—$(CH_2)_o$—X—$(CH_2)_p$—, or —$(CH_2)_n$—X—$(CH_2)_p$—, X is O, NH, N—$C_1$-$C_6$-alkyl or $S(O)_m$, $R^1$ is H, $C_{1-6}$-alkyl, aryl or heteroaryl, Y and A are defined as above, m is a whole number selected from 0, 1, 2 and n, o and p are independently numbers in the range of 0-6.

The compounds of the present invention have at least two chiral carbon atoms and it is to be understood that the invention also encompasses the single enantiomers of the compounds of formula I, racemic mixtures, non-racemic mixtures, diastereomers of the compounds of formula I and mixtures of the diastereomers of the compound of formula I.

Preferred are therefore compounds of formula I above selected from

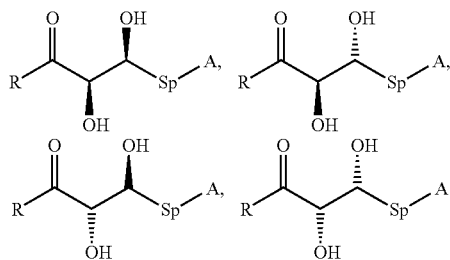

and mixtures thereof, wherein residues R, Sp and A are as defined above.

The compounds of the present invention can be prepared by principally known methods. For example they can be synthesized from the corresponding aldehyde and corresponding hydroxyketone derivative, where hydroxyl groups of the latter can be unprotected or protected by hydroxy protecting groups known in the art, such as phosphate, sulphate, arsenate, silyl, benzyl, acetyl, acetonyl- and other protecting groups. The hydroxyketone could be used in a form as a silyl-, or lithium enolate. The reaction could be catalyzed/promoted by organic or inorganic bases, enzymes (in particular aldolases of type I and II), antibodies, chiral or racemic cyclic secondary amines such as proline, pyrrolidine, piperidine, imidazoline, imidazolinone and their derivatives or acyclic secondary dialkylamines in organic, ionic liquids or aqueous mediums. The reaction could be performed under acid catalyzed conditions using inorganic or organic acids, metal complexes or other Lewis and Brönsted acids. The catalyst may be implemented on polymer or microparticle or the catalyst could be a polymer or microparticle itself. The compounds can also be prepared by a transketolase-catalyzed reaction of a corresponding aldehyde and hydroxypyruvate. Such processes could also be catalysed by compounds containing amino-functionality. How to conduct said reaction is known in the art.

The compounds of the present invention are excellent UV-filters that have essentially the same compatibility with the skin as the substituent A. The compounds do not tend to penetrate into the skin and have a particularly good adhesion to the skin. This makes these compounds particularly suitable as ingredients of sunscreen compositions which could be cosmetic or dermatological compositions. These compositions are generally topical compositions.

The present invention further relates to topical cosmetic or pharmaceutical compositions comprising a compound of the present invention, in particular a topical cosmetic or pharmaceutical composition wherein the compound of the present invention is used as an UV filter. These compositions are preferably sunscreens, moisturizers or tanning lotions.

The present invention also relates to the use of a compound of the present invention as an UV filter, which is preferred, as a skin moisturizer, tanning agent, improvement agent to enhance water resistance of the UV protection or moisturization, and to achieve a long-lasting UV protection, tan or moisturization. Preferably the present invention relates to the use of a compound of the present invention as an UV filter or a tanning agent, in particular as a UV filter.

In one embodiment the present invention relates to the use of a compound of the present invention in combination with dihydroxyacetone (DHA) and/or erytrulose, in particular in self-tanning cosmetics.

The present invention further relates to the use of a compound of the present invention as an UV filter in a sunscreen composition.

The present invention further relates to the use of a compound of the present invention as a tanning agent in a self-tanning composition.

The present invention also relates to a sunscreen composition containing a compound of the present invention, and optionally one or more further UV-filter agents and one or more cosmetically acceptable adjuvants.

For the preparation of the topical sunscreen compositions, especially topical cosmetic and pharmaceutical compositions and preparations for dermatological and/or cosmetic use, such as skin protection and sunscreen formulations for everyday cosmetics the compounds of the present invention can be incorporated in auxiliary agents, e.g. a cosmetic base, which are conventionally used for such formulations. Where convenient, other conventional UV-A and/or UV-B and/or broad spectrum screening agents may also be added. The combination of UV screens may show a synergistic effect. The amount of the compounds of the present invention and other known UV-screens is not critical. Suitable amounts of the compounds of the present invention are about 0.01 to about 50% by weight, preferably about 0.01 to 25 wt. % of the composition. If one or more other UV-filter compounds are present, such additional compounds are hydrophilic and/or lipophilic UV-A or UV-B or broad spectrum screening agents and are present in an amount of preferably about 0.5-12% by weight of the compositions. These additional screening agents are advantageously selected from among the compounds listed below without being limited thereto:

Examples of UV-B or broad spectrum screening agents, i.e. substances having absorption maximums between about 290 and 340 nm, which come into consideration for combination with the compounds of the present invention are for example the following organic and inorganic compounds:

Acrylates such as 2-ethylhexyl 2-cyano-3,3-diphenylacrylate (octocrylene, PARSOL® 340), ethyl 2-cyano-3,3-diphenylacrylate and the like;

Camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, terephthalidene dicamphor sulfonic acid and the like;

Cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bonded to siloxanes;

p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate, Benzophenones such as benzophenone-3, benzophenone-4, 2,2',4,4'-tetrahydroxy-benzophenone, 2,2'-dihydroxy-4,4'-dimethoxybenzophenone and the like;

Esters of Benzalmalonic acid such as di-(2-ethylhexyl) 4-methoxybenzalmalonate;

Esters of 2-(4-ethoxy-anilinomethylene)propandioic acid such as 2-(4-ethoxy anilinomethylene)propandioic acid diethyl ester as described in the European Patent Publication EP 0895 776;

Organosiloxane compounds containing benzmalonate groups as described in the European Patent Publications EP 0358584 B1, EP 0538431 B1 and EP 0709080 A1;

Drometrizole trisiloxane (Mexoryl XL);

Pigments such as microparticulated $TiO_2$, and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like.

Salicylate derivatives such as isopropylbenzyl salicylate, benzyl salicylate, butyl salicylate, octyl salicylate (NEO HELIOPAN OS), isooctyl salicylate or homomethyl salicylate (homosalate, HELIOPAN) and the like;

Triazine derivatives such as octyl triazone (UVINUL T-150), dioctyl butamido triazone (UVASORB HEB), bis ethoxyphenol methoxyphenyl triazine (Tinosorb S) and the like;

Encapsulated UV-filters such encapsulated as methoxycinnamate (Eusolex UV-pearls) and the like.

Examples of broad spectrum or UV A screening agents i.e. substances having absorption maximums between about 320 and 400 nm, which come into consideration for combination with the compounds of the present invention are for example the following organic and inorganic compounds:

Dibenzoylmethane derivatives such as 4-tert. butyl-4'-methoxydibenzoyl-methane (PARSOL® 1789), dimethoxydibenzoylmethane, isopropyldibenzoylmethane and the like;

Benzotriazole derivatives such as 2,2'-methylene-bis-(6-(2H-benzotriazole-2-yl)-4-(1,1,3,3,-tetramethylbutyl)-phenol (TINOSORB M) and the like;

phenylene-1,4-bis-benzimidazolsulfonic acids or salts such as 2,2-(1,4-phenylene)bis-(1H-benzimidazol-4,6-disulfonic acid) (Neoheliopan AP);

amino substituted hydroxybenzophenones such as 2-(4-Diethylamino-2-hydroxy-benzoyl)-benzoic acid hexylester as described in the European Patent Publication EP 1046391

Pigments such as microparticulated ZnO or $TiO_2$ and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g., 3,3-Diphenylacrylate derivatives as described in the European Patent Publications EP 0 514 491 B1 and EP 0 780 119 A1;

Benzylidene camphor derivatives as described in the U.S. Pat. No. 5,605,680;

Organosiloxanes containing benzmalonate groups as described in the European Patent Publications EP 0358584 B1, EP 0538431 B1 and EP 0709080 A1.

The compositions of the invention can also contain usual cosmetic adjuvants and additives, such as preservatives/antioxidants, fatty substances/oils, water, organic solvents, silicones, thickeners, softeners, emulsifiers, additional sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, in particular those suited for providing an additional photoprotective effect by physically blocking out ultraviolet radiation, or any other ingredients usually formulated into cosmetics, in particular for the production of sunscreen/antisun compositions. The necessary amounts of the cosmetic and dermatological adjuvants and additives can, based on the desired product, easily be chosen by a skilled artisan in this field and will be illustrated in the examples, without being limited hereto.

An additional amount of antioxidants/preservatives is generally preferred. Based on the invention all known antioxidants usually formulated into cosmetics can be used. Especially preferred are antioxidants chosen from the group consisting of amino acids (e.g. glycine, histidine, tyrosine, tryptophane) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinsulfoximine, buthioninsulfone, penta-, hexa-, heptathioninsulfoximine) in very low compatible doses (e.g. pmol bis μmol/kg), additionally (metal)-chelators (such as α-hydroxyfatty acids, palmic-, phytinic acid, lactoferrin), β-hydroxy acids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbylacetate), tocopherole and derivates (such as vitamin-E-acetate), mixtures of nat. vitamin E, vitamin A and derivatives (vitamin-A-palmitate and -acetate) as well as coniferylbenzoate, rutinic acid and derivatives, α-glycosylrutin, ferulic acid, furfurylidenglucitol, carnosin, butylhydroxytoluene, butylhydroxyanisole, trihydroxybutyrophenone, urea and its derivatives, mannose and derivatives, zinc and derivatives (e.g. ZnO, $ZnSO_4$), Selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 wt. % to about 10 wt. % of the total weight of the composition of the present invention. Preferably, one or more preservatives/antioxidants are present in an amount about 0.1 wt. % to about 1 wt. %.

Typically formulations also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount about 0.01 wt. % to about 20 wt. % of the total weight of the composition of the present invention. Preferably, about 0.1 wt. % to about 10 wt. % of emulsifiers are used.

The lipid phase can advantageously be chosen from:
mineral oils and mineral waxes;
oils such as triglycerides of caprinic acid or caprylic acid, preferable castor oil;
oils or waxes and other natural or synthetic oils, in an preferred embodiment esters of fatty acids with alcohols e.g. isopropanol, propylene glycol, glycerin or esters of fatty alcohols with carbonic acids or fatty acids;
alkylbenzoates; and/or
silicone oils such as dimethylpolysiloxane, diethylpolysiloxane, diphenylpolysiloxane, cyclomethicones and mixtures thereof.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaureate, n-decyloleat, isooctylstearate, isononylstearate, isononylisononanoate, 2-ethylhexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the formulation of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbonatoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in formulations of the present invention are isoeikosane; neopentylglycoldiheptanoate; propyleneglycol-dicaprylate/dicaprate; caprylic/capric/diglycerylsuccinate; butyleneglycol caprylat/caprat; $C_{12-13}$-alkyllactate; di-$C_{12-13}$ alkyltartrate; triisostearin; dipentaerythrityl hexacaprylat/hexacaprate; propyleneglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the formulation of the present invention can also contain natural vegetable or animal waxes such as bee wax, china wax, bumblebee wax and other waxes of insects as well as shea butter and cocoa butter.

A moisturizing agent may be incorporated into a composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 20 wt. % of the total weight of the composition. The preferred amount of emollient is about 2 wt. % to about 15 wt. %, and most preferably about 4 wt. % to about 10 wt. %.

Moisturizers that bind water, thereby retaining it on the skin surface are called humectants. Suitable humectants can be incorporated into a composition of the present invention such as glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a composition of the present invention, preferably about 1 wt. % to about 5 wt. %.

The composition of the present invention can also contain at least one additional active ingredient selected from anti-wrinkle/anti-atrophy/anti-ageing actives, flavonoids, anti-cellulite agents, tanning actives, skin lightening agents, additional sunscreen actives, particulate matter, hair growth actives, penetration enhancers/delivery agents, skin soothing actives, anti-acne actives, fragrances, dyes and pigments.

Anti-wrinkle/anti-atrophy/anti-ageing actives are disclosed e.g. in WO 2004/037213. Exemplary anti-wrinkle/anti-atrophy/anti-ageing actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, skin peel agents (e.g., phenol and the like), which enhance skin condition and Vitamin A and its derivatives.

Suitable flavonoids are disclosed e.g. in WO 2004/037213 and in U.S. Pat. Nos. 5,686,082 and 5,686,367, all of which are herein incorporated by reference. Flavonoids suitable for use in the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. The term "substituted" as used herein means flavonoids wherein one or more hydrogen atoms of the flavonoid has been independently replaced with hydroxyl, $C_1$-$C_8$ alkyl, $C_1$-$C_4$ alkoxyl, O-glycoside, and the like or a mixture of these substituents.

Anti-cellulite agents are known in the art and include, but are not limited to, xanthine compounds (e.g. caffeine, theophylline, theobromine and aminophylline).

Tanning actives are known in the art. If a tanning active is included with the compositions of the present invention, it is preferably present from approximately 0.1% to 20%. An example of a suitable tanning active is dihydroxyacetone.

Suitable skin lightening agents are disclosed e.g. in WO 2004/037213. When present, the compositions preferably contain from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in WO 95/34280 and WO 95/23780.

Suitable additional sunscreen actives which can be present in the composition of the present invention are disclosed e.g. in WO 2004/037213. As used herein, "sunscreen active" includes both sunscreen agents and physical sunblocks. Suitable sunscreen actives may be organic or inorganic. Inorganic sunscreens useful herein include metallic oxides, in particular titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the composition. A wide variety of conventional organic sunscreen actives are suitable for use herein. Sagarin, et al., at Chapter VIII, pages 189 et seq., of Cosmetics Science and Technology (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propylene glycol esters); cinnamic acid derivatives (menthyl and benzyl esters, α-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

Also particularly useful in the compositions as additional sunscreen actives are such as those disclosed in U.S. Pat. No. 4,937,370 and U.S. Pat. No. 4,999,186. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. A safe and effective amount of the organic sunscreen active is used, typically from about 1% to about 20%, more typically from about 2% to about 10% by weight of the composition. Exact amounts will vary depending upon the sunscreen or sunscreens chosen and the desired Sun Protection Factor (SPF).

Particularly preferred sunscreens are sunscreens on the basis of polysiloxanes such as Parsol SLX, described e.g. in EP 358 584, EP 538 431 and EP 709 080.

Suitable particulate matter is disclosed in WO 2004/037213. These particulates can be coated or uncoated, charged or uncharged. Charged particulate materials are disclosed in U.S. Pat. No. 5,997,887. Particulate materials useful herein include: bismuth oxychloride, iron oxide, mica, mica treated with barium sulfate and $TiO_2$, silica, nylon, polyethylene, talc, styrene, polypropylene, ethylene/acrylic acid copolymer, titanium dioxide iron oxide, bismuth oxychloride, sericite, aluminum oxide, silicone resin, barium sulfate, calcium carbonate, cellulose acetate, polymethyl methacrylate, and mixtures thereof.

Hair growth actives are known in the art. Hair growth actives or stimulants particularly suitable for use in compositions of the present invention may include but are not limited to benzalkonium chloride, benzethonium chloride, phenol, flavanoids, diphenhydramine hydrochloride, chlorophyllin derivatives, cholesterol, salicylic acid, cystine, methionine, red pepper tincture, benzyl nicotinate, dl-menthol, peppermint oil, calcium pantothenate, panthenol, castor oil, hinokitiol, resorcinol, biotin, metabolic intermediates of the urea cycle (WO 94/09750), peptides, metal peptides and peptide derivatives.

Particularly preferred hair growth actives include: α-1,4 esterified disaccharides described in EP-A 0 064 012, esterified oligosaccharides as described in EP-A 0 211 610, minoxidil glucuronides as described in EP 0 242 967, minoxidil sulphates as described in WO 86/04231, minoxidil, and other derivatives thereof as described in U.S. Pat. No. 4,139,619, ethylenediaminetetraacetic acid or salts thereof as described in U.S. Pat. No. 4,814,351, direct proteoglycanase inhibitors such as 1,10-phenanthroline as described in EP 0 277 428, glycosaminoglycanase inhibitors as described in EP 0 277 428 such as D-glucaro-1,4-lactone, glycosaminoglycanase inhibitors, as described in EP 0 277 428 such as N-acetylglucosamine, glycosaminoglycan chain cellular uptake inhibitors as described in EP 0 277 428 such as hexuronic acid and esters thereof, chemical inhibitors of glycosidase activity as described in EP 0 334 586 chosen from lactams, such as D-glucaro-1,5-lactam, chemical activators of protein kinase C enzymes as described in EP 0 334 585 chosen from diacylglycerols such as 1,2-dioleoyl-sn-glycerol, glycosaminoglycanase inhibitors as described in EP 0 348 184 such as 6-methyl-glucaro-1,4-lactone, glycosaminoglycanase inhibitors as described in EP 0 348 184 chosen from acylated monosaccharides such as 2-propionamido-2-deoxyglucose, esters of pyroglutamic acid as described in U.S. Pat. No. 4,774,255 such as pyroglutamic acid n-hexyl ester and pyroglutamic acid n-octyl ester, hexosaccharic acids or acylated hexosaccharic acids, or salts or esters thereof, as described in EP 0 378 388 such as glucosaccharic acid, and its disodium salt, aryl-substituted ethylenes as described in EP 0 403 238 such as 1,1-dicarboxy-2-(4-hydroxyphenyl)ethylene.

Skin soothing actives include panthenoic acid derivatives (including panthenol, dexpanthenol, ethyl panthenol), aloe vera, allantoin, bisabolol and dipotassium glycyrrhizinate. Anti-acne actives include Vitamin C and its derivatives.

If nothing else is stated, the additional active ingredient is present in the compositions of the present invention in an amount of preferably 0.1 to 20, more preferably of 1 to 10 wt.-%, based on the weight of the composition.

The aqueous phase of the compositions of the present invention can contain the usual cosmetic additives such as alcohols, especially lower alcohols, preferably ethanol and/or isopropanol, low diols or polyols and their ethers, preferably propylene glycol, glycerin, ethylene glycol, ethylene glycol monoethyl- or monobutylether, propylene glycol monomethyl- or -monoethyl- or -monobutylether, diethylene glycol monomethyl-or monoethylether and analogue products, polymers, foam stabilizers; electrolytes and especially one or more thickeners. Thickeners that may be used in formulations of the present invention to assist in making the consistency of a product suitable include carbomer, siliciumdioxide, magnesium and/or aluminum silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof. Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the composition of the present invention, preferably, 1 wt. % to about 5 wt. %.

The addition of electrolytes into the composition of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the composition of the present invention.

The compositions of the invention are useful as compositions for photoprotecting the human epidermis or hair against the damaging effect of ultraviolet irradiation, as sunscreen compositions. Such compositions can, in particular, be provided in the form of a lotion, a thickened lotion, a gel, a cream, a milk, an ointment, a powder or a solid tube stick and can be optionally be packaged as an aerosol and can be provided in the form of a mousse, foam or a spray. When the cosmetic composition according to the invention are provided for protecting the human epidermis against UV radiation or as sunscreen composition, they can be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

The following examples are provided to further illustrate the compounds and compositions of the present invention. These examples are illustrative only and are not intended to limit the scope of the invention in any way.

EXAMPLE 1

4-(4-Benzoxazol-2-yl-phenyl)-3,4-dihydroxy-butan-2-one

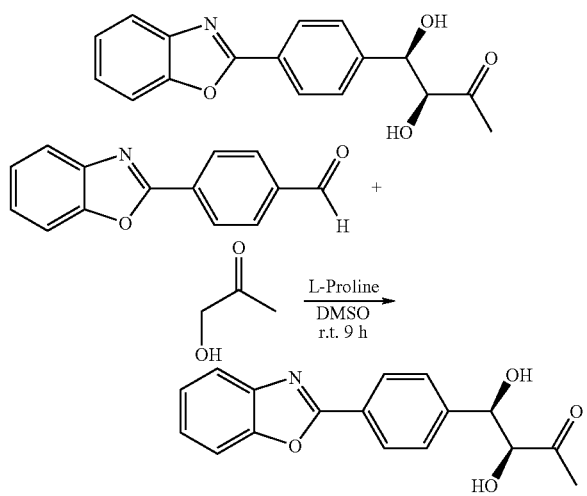

Flame dried 10 mL flask was filled with argon and charged with hydroxyacetone (1 ml) and anhydrous DMSO (2 ml). After solution is formed the 4-benzoxazol-2-yl-benzaldehyde (2.2 mmol) followed by L-Proline (1.1 mmol) were added. The resulted homogeneous reaction mixture was stirred at room temperature for 24 h. Then, half saturated $NH_4Cl$ solution (20 ml) and ethyl acetate (10 ml) was added with vigorous stirring, the layers were separated and the aqueous phase was extracted thoroughly with ethyl acetate (5×10 ml). The combined organic phases were dried ($Na_2SO_4$) and concentrated in vacuum. The residue was recrystallized from EtOH yielding 95 mg of pure product as white crystals; the mother liquor was purified by column chromatography (eluent-ethyl acetate/hexanes-6/3) yielding next 125 mg (total yield 66%) of the pure product.

$^1$H-NMR (300 MHz, DMSO-$d_6$): δ=8.15 (2H, d, J 8.28 Hz, Ph-H), 7.79 (2H, m, benzoxazole-H), 7.62, 7.57 (0.5H+1.5H, d+d, J 8.28 Hz, Ph-H minor and major isomers), 7.41 (2H, m, benzoxazole-H), 5.80 (0.75H, d, J 4.9 Hz, OH major isomer), 5.65 (1H, d, J 5.8, OH), 5.18 (0.25H, d, J 6.8 Hz, OH minor isomer), 5.06 (0.25H, m, CH minor isomer), 4.75 (0.75H, m, major isomer), 4.15 (0.25H, m, CH minor isomer), 3.98 (0.75H, m, major isomer), 2.21 (0.7H, s, $CH_3$ minor isomer), 2.09 (2.3H, s, major isomer).

$^{13}$C-NMR (75 MHz, DMSO-$d_6$): δ=209.6, 162.3, 150.1, 146.6, 141.5, 127.9, 127.4, 126.7, 125.4, 125.1, 124.8, 119.7, 110.8, 80.7, 73.8, 26.8.

MS (LCMS)=298 (M+1).

EXAMPLE 2

4-(4-Benzoxazol-2-yl-phenyl)-1,3,4-trihydroxy-butan-2-one (Compound B)

Compound B was prepared as a mixture of isomers in analogy to example 1 from 4-benzoxazol-2-yl-benzaldehyde and 1,3-dihydroxyacetone.

$^{1}$H-NMR (300 MHz, DMSO-$d_6$+CD$_3$COOD): δ=8.15 (2H, d, J 8.28 Hz, Ph-H), 7.79 (2H, m, benzoxazole-H), 7.62, 7.56 (1.3H+0.7H, d+d, J 8.28 Hz, Ph-H minor and major isomers), 7.41 (2H, m, benzoxazole-H), 5.05 (0.5H, d, J 2.7 Hz, CH), 4.75 (0.3H, d, J 6.6 Hz, CH), 4.37, 4.32 (2H, s, CH$_2$), 4.28 (0.5H, J, 2.7 Hz, CH), 4.14 (0.3H, d, CH), 4.10 (0.4H, d, CH).

$^{13}$C-NMR (75 MHz, DMSO-$d_6$): δ=211.6, 162.3, 150.1, 146.8, 141.5, 127.9, 127.5, 126.7, 125.4, 124.9, 119.7, 110.8, 79.2, 73.1, 66.5.

MS (LCMS)=314 (M+1).

EXAMPLE 3

Skin Binding Experiment

The skin binding properties were determined by the following experiment. Skin samples (1 cm² each) were prepared by punching out from pig ear. The skin samples were placed in a 2 mL eppendorf plastic tube. The studied compounds were applied topically as a 2% (w) THF solution on the skin surface at a mean dose rate of 1 mg/cm². The samples were placed in a heatingblock and maintained at a normal skin temperature of 32±1° C. for the duration of the exposure period. At the end of the experiment, after 24 hours, respectively 72 h, each skin probe was extracted by shaking with 1000 μl of THF for 1 min and the resulting solution was analyzed by HPLC. The experiments were run in duplicates.

Compounds B and was tested for their skin-binding capacity, while compound A (described in Kawashita, Y; Nakamichi, N.; Kawabata, H.; Hayashi, M. *Org. Lett.* 2003, 5, 3713-3715) was used as a non-binding reference.

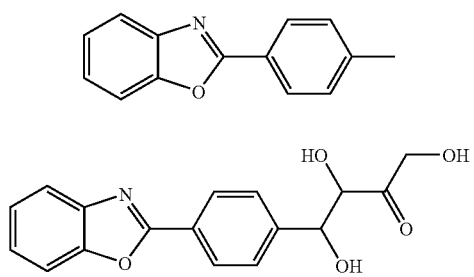

A

B

Analytical Method: High Performance Liquid Chromatography

Skin fraction samples were injected into the HPLC system using DAD detection with the following conditions:

| | |
|---|---|
| HPLC system | Agilent 1100 Series |
| Software | Agilent ChemStation Plus Family LC-MS$^{3D}$ 8.03 (Windows NT) |
| Column | Eclipse ® XDB C8 5 μm, 4.6 × 150 |
| Mobile Phase | 0.1% trifluoroacetic acid in water/Acetonitril. Start (100/0, v/v), 8 min (20/80 v/v), 15 min (0/100 v/v) |
| Flow | 1.000 ml/min |
| Injection volume | 20 μl |
| Detection wavelength | 310 nm |
| Retention time | approx. 6.1 and 6.2(min) for both diastereomers |
| Analysis time | 17 min |

The % of UV filter bound to the skin was determined by calculation of the recovery rate using the following equation:

$$\% \ UV\text{-filter bound} = \frac{\text{Mean amount bound } (\mu g/cm^2)}{\text{Mean amount applied } (\mu g/cm^2)} \times 100$$

Results:

| | % UV filter bound to the skin | |
|---|---|---|
| | After 24 h | After 72 h |
| Compound A | 36.3 | 61.1 |
| Compound B | 96.6 | 100 |

As can be seen from the results, compound B exhibits a significant adhesion to the skin compared to the non-binding compound A. It should be noted that due to a penetration of compound A into the skin and insufficient removing of the entire compound from the sample and tube, the recovery of compound A is not 100% as expected.

EXAMPLE 4

O/W Sun Milk

| Ingredients | INCI Nomenclature | % w/w |
|---|---|---|
| A) 4-(4-Benzoxazol-2-yl-phenyl)-1,3,4-trihydroxy-butan-2-one | | 6.00 |
| PARSOL 1789 | Butyl Methoxydibenzoylmethane | 2.00 |
| Lanette O | Cetearyl Alcohol | 2.00 |
| Myritol 318 | Caprylic/capric Triglyceride | 6.00 |
| Mineral oil | Mineral oil | 2.00 |
| Vitamin E acetate | Tocopheryl Acetate | 1.00 |
| Prisorine 3515 | Isostearyl Alcohol | 4.00 |
| B) Edeta BD | Disodium EDTA | 0.10 |
| Neo Heliopan AP | | 3.00 |
| Phenonip | Phenoxyethanol & Methylparaben & Ethylparaben & Propylparaben & Butylparaben | 0.60 |
| Amphisol K | Potassium Cetyl Phosphate | 2.00 |
| Water deionized | Aqua | ad 100 |
| 1,2-Propylen Glycol | Propylene Glycol | 5.00 |
| Carbopol 981 | Carbomer | 0.30 |
| Tinosorb M | Methylene Bis-Benzotriazolyl Tetramethylbutylphenol | 6.00 |
| KOH 10% solution | Potassium Hydroxyde | 2.10 |
| C) 'Double coated titanium dioxide' | | 0.01-25 |

Procedure:

Heat part A) and B) to 85° C. separately while stirring. When homogeneous, add part B) to A) under agitation. Cool to ambient temperature while stirring and add part C). Homogenize to achieve a small particle size.

EXAMPLE 5

O/W Sun Milk

| | Ingredients | INCI Nomenclature | % w/w |
|---|---|---|---|
| A) | 4-(4-Benzoxazol-2-yl-phenyl)-1,3,4-trihydroxy-butan-2-one | | 3.00 |
| | Uvinul A Plus | Diethylamino Hydroxybenzoyl Hexyl Benzoate | 2.00 |
| | Lanette O | Cetearyl Alcohol | 2.00 |
| | Myritol 318 | Caprylic/capric Triglyceride | 6.00 |
| | Mineral oil | Mineral oil | 2.00 |
| | Vitamin E acetate | Tocopheryl Acetate | 1.00 |
| | Prisorine 3515 | Isostearyl Alcohol | 4.00 |
| B) | Edeta BD | Disodium EDTA | 0.10 |
| | Neo Heliopan AP | | 3.00 |
| | Phenonip | Phenoxyethanol & Methylparaben & Ethylparaben & Propylparaben & Butylparaben | 0.60 |
| | Amphisol K | Potassium Cetyl Phosphate | 2.00 |
| | Water deionized | Aqua | ad 100 |
| | 1,2-Propylen Glycol | Propylene Glycol | 5.00 |
| | Carbopol 981 | Carbomer | 0.30 |
| | Tinosorb M | Methylene Bis-Benzotriazolyl Tetramethylbutylphenol | 6.00 |
| | KOH 10% solution | Potassium Hydroxyde | 2.10 |
| C) | 'Double coated titanium dioxide' | | 0.01-25 |

Procedure:

Heat part A) and B) to 85° C. separately while stirring. When homogeneous, add part B) to A) under agitation. Cool to ambient temperature while stirring and add part C). Homogenize to achieve a small particle size.

EXAMPLE 6

Sun Milk Waterproofed

| | Ingredients | INCI Nomenclature | % w/w |
|---|---|---|---|
| A) | 4-(4-Benzoxazol-2-yl-phenyl)-1,3,4-trihydroxy-butan-2-one | | 3.00 |
| | PARSOL 1789 | Butyl Methoxydibenzoylmethane | 2.00 |
| | PARSOL 5000 | 4-Methylbenzylidene Camphor | 4.00 |
| | Uvinul T 150 | Ethylhexyltriazone | 2.00 |
| | Silicone DC 200/350 cs | Dimethicone | 1.00 |
| | Lanette O | Cetearyl Alcohol | 2.00 |
| | Softisan 100 | Hydrogenated Coco-Glycerides | 3.00 |
| | Tegosoft TN | C12-15 Alkyl Benzoate | 6.00 |
| | Cetiol B | Dibutyl Adipate | 7.00 |
| | Vitamin E acetate | Tocopheryl Acetate | 2.00 |
| | BHT | BHT | 0.05 |
| | Edeta BD | Disodium EDTA | 0.10 |
| | Phenonip | Phenoxyethanol & Methylparaben & Ethylparaben & Propylparaben & Butylparaben | 1.00 |
| | Amphisol K | Cetyl Phosphate potassium | 2.00 |
| B) | Water deionized | Aqua | ad 100 |
| | Propylene Glycol | Propylene Glycol | 5.00 |
| | Carbopol 980 | Carbomer | 0.30 |
| | KOH (10% sol.) | Potassium Hydroxide | 1.50 |
| C) | 'Double coated titanium dioxide' | | 0.01-25 |

Procedure:

Heat part A) and B) to 85° C. separately while stirring. When homogeneous, add part B) to A) under agitation. Cool to ambient temperature while stirring and add part C). Homogenize to achieve a small particle size.

EXAMPLE 7

High SPF Sun Milk

| | Ingredients | INCI Nomenclature | % w/w |
|---|---|---|---|
| A) | 4-(4-Benzoxazol-2-yl-phenyl)-1,3,4-trihydroxy-butan-2-one | | 3.00 |
| | PARSOL 1789 | Butyl Methoxydibenzoylmethane | 2.00 |
| | PARSOL 5000 | 4-Methylbenzylidene Camphor | 4.00 |
| | Uvinul T 150 | Octyl Triazone | 2.00 |
| | Silicone DC 200/350 cs | Dimethicone | 1.00 |
| | Lanette O | Cetearyl Alcohol | 2.00 |
| | Softisan 100 | Hydrogenated Coco-Glycerides | 3.00 |
| | Tegosoft TN | C12-15 Alkyl Benzoate | 6.00 |
| | Cetiol B | Dibutyl Adipate | 7.00 |
| | Vitamin E acetate | Tocopheryl Acetate | 2.00 |
| | BHT | BHT | 0.05 |
| | Edeta BD | Disodium EDTA | 0.10 |
| | Phenonip | Phenoxyethanol & Methylparaben & Ethylparaben & Propylparaben & Butylparaben | 0.60 |
| | Amphisol K | Potassium Cetyl Phosphate | 2.00 |
| B) | Water deionized | Aqua | ad 100 |
| | Propylene Glycol | Propylene Glycol | 5.00 |
| | Carbopol 980 | Carbomer | 0.30 |
| | KOH (10% sol.) | Potassium Hydroxide | 1.50 |
| C) | 'Double coated titanium dioxide' | | 0.01-25 |
| D) | Perfume | Perfume | q.s. |

Procedure:

Heat part A) and B) to 85° C. separately while stirring. When homogeneous, add part B) to A) under agitation. Cool to ambient temperature while stirring and add part C) and D). Homogenize to achieve a small particle size.

EXAMPLE 8

Water-Free Sun Gel

| | Ingredients | INCI Nomenclature | % w/w |
|---|---|---|---|
| A) | 4-(4-Benzoxazol-2-yl-phenyl)-1,3,4-trihydroxy-butan-2-one | | 6.00 |
| | PARSOL 1789 | Butyl Methoxydibenzoylmethane | 4.00 |
| | PARSOL 5000 | 4-Methylbenzylidene Camphor | 4.00 |
| | Uvasorb HEB | Diethylhexyl Butamido Triazone | 1.50 |

| Ingredients | INCI Nomenclature | % w/w |
|---|---|---|
| Vitamin E acetate | Tocopheryl Acetate | 1.50 |
| Tegosoft TN | C12-15 Alkyl Benzoate | 9.00 |
| Elefac I-205 | Ethylhexyldodecyl Neopentanoate | 2.00 |
| Alcohol | Alcohol | ad 100 |
| Isopropyl Alcohol | Isopropyl Alcohol | 20.00 |
| B) Klucel MF | Hydroxypropylcellulose | 2.00 |
| C) 'Double coated titanium dioxide' | | 0.01-25 |
| D) perfume | | q.s. |

Procedure:

Mix part A) and B) while stirring. When homogeneous, add part C) and D) under agitation.

EXAMPLE 9

Sun Gel

| | Ingredients | INCI Nomenclature | % w/w |
|---|---|---|---|
| A) | Pemulen TR-2 | Acrylates/C10-30 Alky Acrylate Crosspolymer | 0.60 |
| | Phenonip | Phenoxyethanol & Methylparaben & Ethylparaben & Propylparaben & Butylparaben | 0.60 |
| | Edeta BD | Disodium EDTA | 0.1 |
| | Aqua | Aqua | ad 100 |
| B) | 4-(4-Benzoxazol-2-yl-phenyl)-1,3,4-trihydroxy-butan-2-one | | 4.00 |
| | PARSOL 340 | Octocrylene | 3.00 |
| | Tegosoft TN | C12-15 Alkyl Benzoate | 15.00 |
| | Antaron V-216 | PVP/Hexadecene Copolymer | 1.00 |
| | Vitamin E acetate | Tocopheryl Acetate | 0.50 |
| | Butylated Hydroxytoluene | BHT | 0.05 |
| | Cremophor RH 410 | PEG-40 Hydrogenated Castor Oil | 0.50 |
| | Tris Amino | Tromethamine | 0.50 |
| C) | 'Double coated titanium dioxide' | | 0.01-25 |
| D) | Perfume | Perfume | q.s. |

Procedure:

Heat part A) and B) to 85° C. separately while stirring. When homogeneous, add part B) to A) under agitation. Cool to ambient temperature while stirring and add part C) and D). Homogenize to achieve a small particle size.

EXAMPLE 10

High Protection W/O Sun Milk

| | Ingredients | INCI Nomenclature | % w/w |
|---|---|---|---|
| A) | PARSOL 1789 | Butyl Methoxydibenzoylmethane | 2.00 |
| | 4-(4-Benzoxazol-2-yl-phenyl)-1,3,4-trihydroxy-butan-2-one | | |
| | Uvinul T 150 | Ethylhexyl Triazone | 2.00 |
| | Arlacel P 135 | PEG-30 Dipolyhydroxystearate | 2.00 |
| | Tegosoft TN | C12-15 Alkyl Benzoate | 5.00 |
| | Cosmacol EMI | Di-C12-13 Alkyl Malate | 6.00 |
| | Miglyol 840 | Propylene Glycol Dicaprylate/Dicaprate | 6.00 |
| | Butylated Hydroxytoluene | BHT | 0.05 |
| | Phenonip | Phenoxyethanol & Methylparaben & Ethylparaben & Propylparaben & Butylparaben | 0.60 |
| B) | Deionized water | Aqua | ad 100 |
| | Glycerin | Glycerin | 5.00 |
| | Edeta | Disodium EDTA | 0.1 |
| | NaCl | Sodium Chloride | 0.30 |
| C) | PARSOL HS | Phenylbenzyimidazole Sulphonic Acid | 4.00 |
| | Water | Aqua | 20.00 |
| | Triethanolamine 99%. | Triethanolamine | 2.50 |
| D) | 'Double coated titanium dioxide' | | 0.01-25 |
| E) | Perfume | | q.s. |

Procedure:

Heat part A), B) and C) to 85° C. separately while stirring. When homogeneous, add part B) and C) to A) under agitation. Cool to ambient temperature while stirring and add part D) and E). Homogenize to achieve a small particle size.

EXAMPLE 11

W/O Milk with Pigments

| | Ingredients | INCI Nomenclature | % w/w |
|---|---|---|---|
| A) | Cremophor WO 7 | PEG-7 Hydrogenated Castor Oil | 6.00 |
| | Elfacos ST 9 | PEG-45/Dodecyl Glycol Copolymer | 2.00 |
| | PARSOL 1789 | Butyl Methoxydibenzoylmethane | 3.00 |
| | Tinosorb S | Bis-Ethylhexyloxyphenol Methoxyphenol Trazine | 5.00 |
| | 4-(4-Benzoxazol-2-yl-phenyl)-1,3,4-trihydroxy-butan-2-one | | 4.00 |
| | microfine ZnO | Zinc Oxide | 2.00 |
| | Microcrystalline wax | Microcrystalline Wax | 2.00 |
| | Miglyol 812 | Caprylic/capric Triglyceride | 5.00 |
| | Vitamin E acetate | Tocopheryl Acetate | 1.00 |
| | Jojoba oil | *Simmondsia Chinensis* Seed Oil | 5.00 |
| | Edeta BD | Disodium EDTA | 0.10 |
| | Butylated Hydroxytoluene | BHT | 0.05 |
| | Phenonip | Phenoxyethanol & Methylparaben & Ethylparaben & Propylparaben & Butylparaben | 0.60 |
| B) | Water deionized | Aqua | ad 100 |
| | Glycerin | Glycerin | 5.00 |
| C) | Neo Heliopan AP | | 2.00 |
| | Water deionized | Aqua | 20.00 |
| | KOH 10% solution | Potassium Hydroxide | 4.00 |
| D) | 'Double coated titanium dioxide' | | 0.01-25 |
| E) | Perfume | Perfume | q.s. |

27

Procedure:

Heat part A), B) and C) to 85° C. separately while stirring. When homogeneous, add part B) and C) to A) under agitation. Cool to ambient temperature while stirring and add part D) and E). Homogenize to achieve a small particle size.

EXAMPLE 12

Protective Day Cream with Vitamin C

| | Ingredients | INCI Nomenclature | % w/w |
|---|---|---|---|
| A) | PARSOL SLX | Polysilicone-15 | 2.50 |
| | 4-(4-Benzoxazol-2-yl-phenyl)-1,3,4-trihydroxy-butan-2-one | | 1.50 |
| | Glyceryl Myristate | Glyceryl Myristate | 2.00 |
| | Cetyl Alcohol | Cetyl Alcohol | 0.50 |
| | Myritol 318 | Caprylic/Capric Triglyceride | 5.00 |
| | Crodamol DA | Diisopropyl Adipate | 5.00 |
| | Vitamin E acetate | Tocopheryl Acetate | 2.00 |
| | Butylated Hydroxytoluene | BHT | 0.05 |
| | Phenonip | Phenoxyethanol & Methylparaben & Ethylparaben & Propylparaben & Butylparaben | 0.60 |
| | Edeta BD | Disodium EDTA | 0.10 |
| | Amphisol K | Potassium Cetyl Phosphate | 2.00 |
| B) | Water deionized | Aqua | ad 100 |
| | 1,2-Propylene Glycol | Propylene Glycol | 2.00 |
| | D-Panthenol 75 L | Panthenol | 2.00 |
| | Ethanol | Ethanol | 5.00 |
| | Allantoin | Allantoin | 0.20 |
| | Carbopol ETD 2001 | Carbomer | 0.30 |
| | KOH 10% sol. | Potassium Hydroxide | 1.50 |
| C) | Water | Aqua | 10.00 |
| | Stay-C 50 | Sodium Ascorbyl Phosphate | 0.50 |
| D) | 'Double coated titanium dioxide' | | 0.01-25 |
| E) | Perfume | Perfume | q.s. |

EXAMPLE 13

Photostable O/W Sun Milk

| | Ingredients | INCI Nomenclature | % w/w |
|---|---|---|---|
| A) | PARSOL 1789 | Butyl Methoxydibenzoylmethane | 2.00 |
| | PARSOL 340 | Octocrylene | 1.80 |
| | 4-(4-Benzoxazol-2-yl-phenyl)-1,3,4-trihydroxy-butan-2-one | | 2.00 |
| | PARSOL SLX | Polysilicone-15 | 3.00 |
| | Lanette O | Cetearyl Alcohol | 2.00 |
| | Myritol 318 | Caprylic/capric Triglyceride | 6.00 |
| | Mineral oil | Mineral oil | 2.00 |
| | Vitamin E acetate | Tocopheryl Acetate | 1.00 |
| | Prisorine 3515 | Isostearyl Alcohol | 4.00 |
| B) | Edeta BD | Disodium EDTA | 0.10 |
| | Phenonip | Phenoxyethanol & Methylparaben & Ethylparaben & Propylparaben & Butylparaben | 0.60 |
| | Amphisol K | Potassium Cetyl Phosphate | 2.00 |
| | Water deionized | Aqua | ad 100 |
| | 1,2-Propylen Glycol | Propylene Glycol | 5.00 |
| | Carbopol 981 | Carbomer | 0.30 |

28

-continued

| | Ingredients | INCI Nomenclature | % w/w |
|---|---|---|---|
| | KOH 10% solution | Potassium Hydroxyde | 2.10 |
| C) | 'Double coated titanium dioxide' | | 0.01-25 |

Procedure:

Heat part A) and B) to 85° C. separately while stirring. When homogeneous, add part B) to A) under agitation. Cool to ambient temperature while stirring and add part C). Homogenize to achieve a small particle size.

The invention claimed is:

1. A compound of formula I:

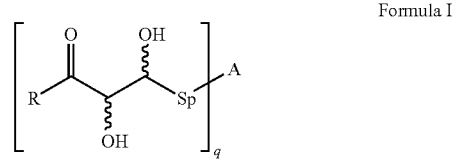

Formula I wherein

R is $C_1$-$C_{24}$-alkyl, optionally substituted with up to 3 hydroxyl groups, a residue —$(CH_2)_n$—Y or residue —$(CH_2)_n$-Sp-A, wherein the —$(CH_2)_n$— moieties can optionally be substituted with up to 3 hydroxyl groups, A is a substituent that absorbs light in the UV-range and has a conjugated π electron system of at least 4π electrons, Sp is a bond or a linear or branched residue —$(CH_2)_n$—, —$(CH_2)_n$—$C_6H_4$—$(CH_2)_o$—, —$(CH_2)_n$—C(=O)—$(CH_2)_o$—, —$(CH_2)_n$—C(=O)—$(CH_2)_o$—X—$(CH_2)_p$—, or —$(CH_2)_n$—X—$(CH_2)_p$—, X is O, $NR^1$, $S(O)_m$, $R^1$ is H, $C_{1-24}$-alkyl, optionally substituted with up to 3 hydroxyl groups, or —$(CH_2)_n$—Y, Y is selected from $C_{1-24}$-alkyl, $C_3$-$C_{10}$-cycloalkyl and $C_6$-$C_{10}$-Aryl, unsubstituted or substituted with 1-3 substituents independently selected from hydroxyl groups and $C_1$-$C_6$-alkyl groups, m is a number selected from 0, 1, 2, n, o and p are whole numbers independently selected from the range of 0-24, and q is 1, and wherein the substituent A is selected from:

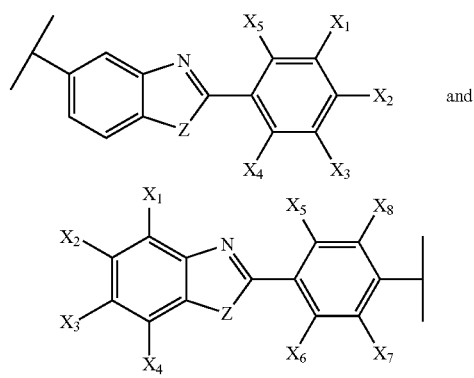

wherein $X_1$, $X_2$, $X_3$, $X_4$, $X_5$, $X_6$, $X_7$ and $X_8$ are independently from each other H, OH, $C_{1-24}$-alkyl, unsubstituted or substituted with up to 3 hydroxyl groups or residues Y, $C_{1-24}$-alkyl-C(O)O, C(O)O—$C_{1-24}$-alkyl, $C_{1-8}$-alkoxyl, S(O)$_r$OH or monoglycosidyl, Z is selected from $NR^2$, O and S, $R^2$ is H, $C_{1-24}$-alkyl, aryl, heteroaryl or Y, Y is as defined previously; and r is 1 or 2.

2. The compound according to claim 1 wherein R is $C_1$-$C_6$-alkyl, optionally substituted with up to 3 hydroxyl groups, —$(CH_2)_n$—Y or a group $(CH_2)_n$-Sp-A (wherein moiety $(CH_2)_n$ is optionally substituted with up to 3 hydroxyl groups), Sp is a bond or a group —$(CH_2)_n$—, —$(CH_2)_n$—$C_6H_4$—$(CH_2)_o$—, —$(CH_2)_n$—C(=O)—$(CH_2)_o$—, —$(CH_2)_n$—C(=O)—$(CH_2)_o$—X—$(CH_2)_p$—, or —$(CH_2)_n$—X—$(CH_2)_p$—, X is O, NH, N—$C_1$-$C_6$-alkyl or S(O)$_m$, $R^1$ is H or $C_{1-6}$-alkyl, Y and A are as defined previously, m is a whole number selected from 0, 1, 2 and n, o and p are independently whole numbers in the range of 0-6.

3. The compound according to claim 1 wherein R is $C_1$-$C_6$-alkyl substituted with one hydroxyl group.

4. The compound according to claim 3 wherein R is a hydroxymethyl group.

5. The compound according to claim 1 wherein Sp is a bond.

6. The compound according to claim 1, wherein the residue Z of substituent A is O and residues $X_1$, $X_2$, $X_3$, $X_4$, $X_5$, $X_6$, $X_7$ and $X_8$ are independently of each other H or $C_1$-$C_6$-alkyl.

7. The compound according to claim 6 wherein residues $X_1$, $X_2$, $X_3$, $X_4$, $X_5$, $X_6$, $X_7$ and $X_8$ are H.

8. The compound according to claim 1 wherein the compound of formula 1 is selected from:

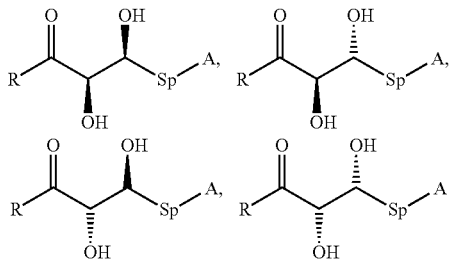

and wherein residues R, Sp and A are as defined previously.

9. A topical cosmetic or pharmaceutical composition comprising a compound according to claim 1.

10. The topical cosmetic or pharmaceutical composition according to claim 9 which is a sunscreen, moisturizer, tanning lotion, or self-tanning cosmetic composition.

11. The topical cosmetic or pharmaceutical composition according to claim 10, containing one or more further UV filter agents and one or more cosmetically acceptable adjuvants.

12. A UV-filter and/or tanning agent which comprises the compound as defined in claim 1.

13. A skin moisturizer, tanning lotion, improvement agent to enhance water resistance of UV protection or moisturization and/or to achieve a long lasting UV protection, tan or moisturization which comprises the compound as defined in claim 1.

14. A self-tanning cosmetic formulation which comprise the compound as defined in claim 1, and at least one dihydroxyaceton (DHA) and erythrulose.

15. A sunscreen composition comprising a UV-filter which includes a compound as defined in claim 1.

16. A composition comprising mixtures of the following compounds:

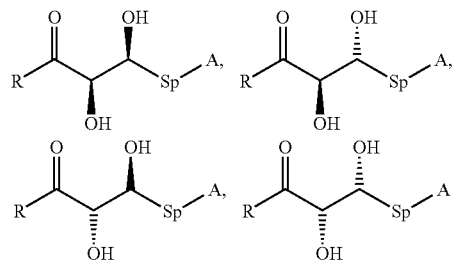

wherein

R is $C_1$-$C_{24}$-alkyl, optionally substituted with up to 3 hydroxyl groups, a residue —$(CH_2)_n$—Y or residue $(CH_2)_n$-Sp-A, wherein the —$(CH_2)_n$— moieties can optionally be substituted with up to 3 hydroxyl groups, A is a substituent that absorbs light in the UV-range and has a conjugated π electron system of at least 4π electrons, and Sp is a bond or a linear or branched residue —$(CH_2)_n$—, —$(CH_2)_n$—$C_6H_4$—$(CH_2)_o$—, —$(CH_2)_n$—C(=O)—$(CH_2)_o$—, —$(CH_2)_n$—C(=O)—$(CH_2)_o$—X—$(CH_2)_p$—, or —$(CH_2)_n$—X—$(CH_2)_p$—.

* * * * *